(12) United States Patent
Wiederin

(10) Patent No.: US 8,925,375 B1
(45) Date of Patent: Jan. 6, 2015

(54) MULTIPLE LOOP SAMPLE INTRODUCTION APPARATUS

(75) Inventor: Daniel R. Wiederin, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 908 days.

(21) Appl. No.: 13/037,956

(22) Filed: Mar. 1, 2011

Related U.S. Application Data

(60) Provisional application No. 61/309,172, filed on Mar. 1, 2010.

(51) Int. Cl.
| | | |
|---|---|---|
| *G01N 1/10* | (2006.01) | |
| *G01N 1/38* | (2006.01) | |
| *G01N 30/20* | (2006.01) | |
| *G01N 35/10* | (2006.01) | |

(52) U.S. Cl.
USPC ... 73/61.55; 73/61.56; 73/863.71; 73/864.22; 73/864.84

(58) Field of Classification Search
CPC .......... G01N 35/1097; G01N 2030/027; G01N 2030/201; G01N 2030/207–2030/208
USPC ........... 73/61.55–61.56, 863.71–863.73, 73/864.21–864.22, 864.25, 864.86–864.84
See application file for complete search history.

(56) References Cited

U.S. PATENT DOCUMENTS

| | | | | | |
|---|---|---|---|---|---|
| 4,710,355 | A | * | 12/1987 | Ushikubo | .......... G01N 35/1097 |
| 5,449,064 | A | * | 9/1995 | Hogan et al. | .................. 204/603 |
| 5,783,740 | A | * | 7/1998 | Tawarayama et al. | .................. G01N 35/1097 |
| 6,638,481 | B2 | * | 10/2003 | Sklar et al. | ....................... 422/63 |
| 6,641,783 | B1 | * | 11/2003 | Pidgeon et al. | .................. 422/70 |
| 7,201,072 | B1 | * | 4/2007 | Wiederin et al. | ........... 73/864.25 |
| 7,343,779 | B1 | * | 3/2008 | Yu | ................. 73/23.41 |
| 7,469,606 | B1 | * | 12/2008 | Wiederin | ................... 73/864.24 |

FOREIGN PATENT DOCUMENTS

JP            2010044006 A   *   2/2010   .............. G01N 35/10

* cited by examiner

*Primary Examiner* — Thomas P Noland
(74) *Attorney, Agent, or Firm* — Advent, LLP

(57) ABSTRACT

A multiple loop sample introduction system comprises a valve assembly including a sample collection valve and a sample introduction valve. First and second sample loops are in fluid communication with the sample collection valve and the sample introduction valve to receive aliquots of liquid samples to be introduced into a nebulizer. The valve assembly is operable to port a first aliquot into the first sample loop, while porting a second aliquot received in the second sample loop for introduction into the nebulizer.

18 Claims, 4 Drawing Sheets

MULTIPLE LOOP SAMPLE INTRODUCTION APPARATUS

PRIORITY

This Nonprovisional application claims the benefit of U.S. Provisional Application Ser. No. 61/309,172 (filed Mar. 1, 2010) under 35 U.S.C. §119(e), herein incorporated by reference in its entirety.

FIELD OF THE INVENTION

The present invention relates generally to laboratory instrumentation, particularly automated sampling devices for drawing samples from stationary sample vessels, and more specifically, to an automated sampling device capable of handling multiple samples at one time.

BACKGROUND OF THE INVENTION

Inductively coupled plasma (ICP) spectrometry is an analysis technique commonly used to determine trace element concentrations and isotope ratios in liquid samples. ICP Spectrometry employs electromagnetically generated partially ionized argon plasma which reaches a temperature of approximately 7000K. When a sample is introduced to the plasma, the high temperature causes sample atoms to become ionized or emit light. Since each chemical element produces a characteristic mass or emission spectrum, measuring the spectra of the emitted light allows the determination of the elemental composition of the original sample.

Sample introduction systems may introduce liquid samples into ICP spectrometry instrumentation (e.g., an inductively coupled plasma mass spectrometer (ICP/ICPMS), an inductively coupled plasma atomic emission spectrometer (ICPAES), or the like, for analysis. For example, a sample introduction system may withdraw an aliquot of a liquid sample from a container and thereafter transport the aliquot to a nebulizer that converts the aliquot into a polydisperse aerosol suitable for ionization in plasma by ICP spectrometry instrumentation. The aerosol is then sorted in a spray chamber to remove larger aerosol particles. Upon leaving the spray chamber, the aerosol enters the ICPMS or ICPAES instrument for analysis. Often, the sample introduction is automated, introducing large numbers of samples into the ICP spectrometry instrumentation in an efficient manner. However, automated sample introduction mechanisms are limited because sample introduction systems can only collect and introduce one sample at a time. The inability of conventional sample introduction systems to simultaneously process more than one sample limits the overall throughput of the system.

Consequently, it would be advantageous if an automated sample introduction apparatus existed that was suitable for collecting and introducing more than one liquid sample at a time.

SUMMARY OF THE INVENTION

Accordingly, the present invention is directed to a novel automated sample introduction method and apparatus for collecting and introducing more than one liquid sample at a time.

The present invention relates to a multiple loop sample introduction system. In the context of this disclosure, the term "sample loop" should be understood to refer to an element configured to hold an aliquot of liquid sample and to act as a conduit in porting the aliquot of liquid sample. In an implementation, the sample introduction system comprises a valve assembly including a sample collection valve and a sample introduction valve. First and second sample loops are ported between/in fluid communication with the sample collection valve and the sample introduction valve to receive aliquots of liquid sample to be introduced into a nebulizer. The valve assembly is operable to receive a first aliquot into the first sample loop while transporting a second aliquot received in the second loop for introduction into a nebulizer.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

Conventional sample introduction systems employ a sample loop to receive and hold aliquots of liquids for introduction into a nebulizer. Such sample introduction systems operate in a sequential manner. Thus, an aliquot of a sample received within the sample loop must be introduced into a nebulizer before an aliquot of the next sample can be drawn in the loop. This sequential manner of operation limits the sample throughput of the system. Moreover, to reduce cross-contamination, the components of the sample introduction system which come into contact with samples, such as the sample loop, autosampler probe, capillary, nebulizer, and so on, are rinsed each time an aliquot of sample is taken. Rinsing of the sample loop adds to the amount of time required to analyze each sample, further limiting the sample throughput of the system.

Accordingly, a multiple loop sample introduction system is described. In one or more implementations, the sample introduction system may comprise a valve assembly including at least a sample collection valve ported to/in fluid communication with a probe of an autosampler. The multiple loop sample introduction system may also include a sample introduction valve in fluid communication with a nebulizer. First and second sample loops may be coupled between the sample collection valve and the sample introduction valve to receive aliquots of liquid samples withdrawn from sample containers by the autosampler. The valve assembly alternates between porting an aliquot of sample into the first sample loop, while concurrently porting an aliquot of sample in the second sample loop for introduction into the nebulizer, and porting an aliquot of sample into the second sample loop, while concurrently porting the aliquot of sample received in the first sample loop for introduction in the nebulizer. In Embodiments, the valve assembly is further operable to port a rinse fluid through each sample loop before receiving the sample while the aliquot of sample contained in the other sample loop is introduced into the nebulizer.

The multiple loop sample introduction system thus withdraws an aliquot of the first sample from a sample container while concurrently introducing an aliquot of a second sample into the nebulizer. In this manner, the sample introduction system provides increased sampling throughput (e.g., analysis of an increased number of samples in a given period of time) in comparison to sample introduction systems that employ a single loop. Additionally, the arrangement of the valve assembly allows the amount of sample withdrawn from sample containers to be reduced. For example, the capillary of the autosampler probe may be shortened, reducing the amount of sample that is withdrawn from each sample container to fill the sample loops. Use of a shorter capillary also reduces memory effects and absorption of sample by the system.

Figure 1A:
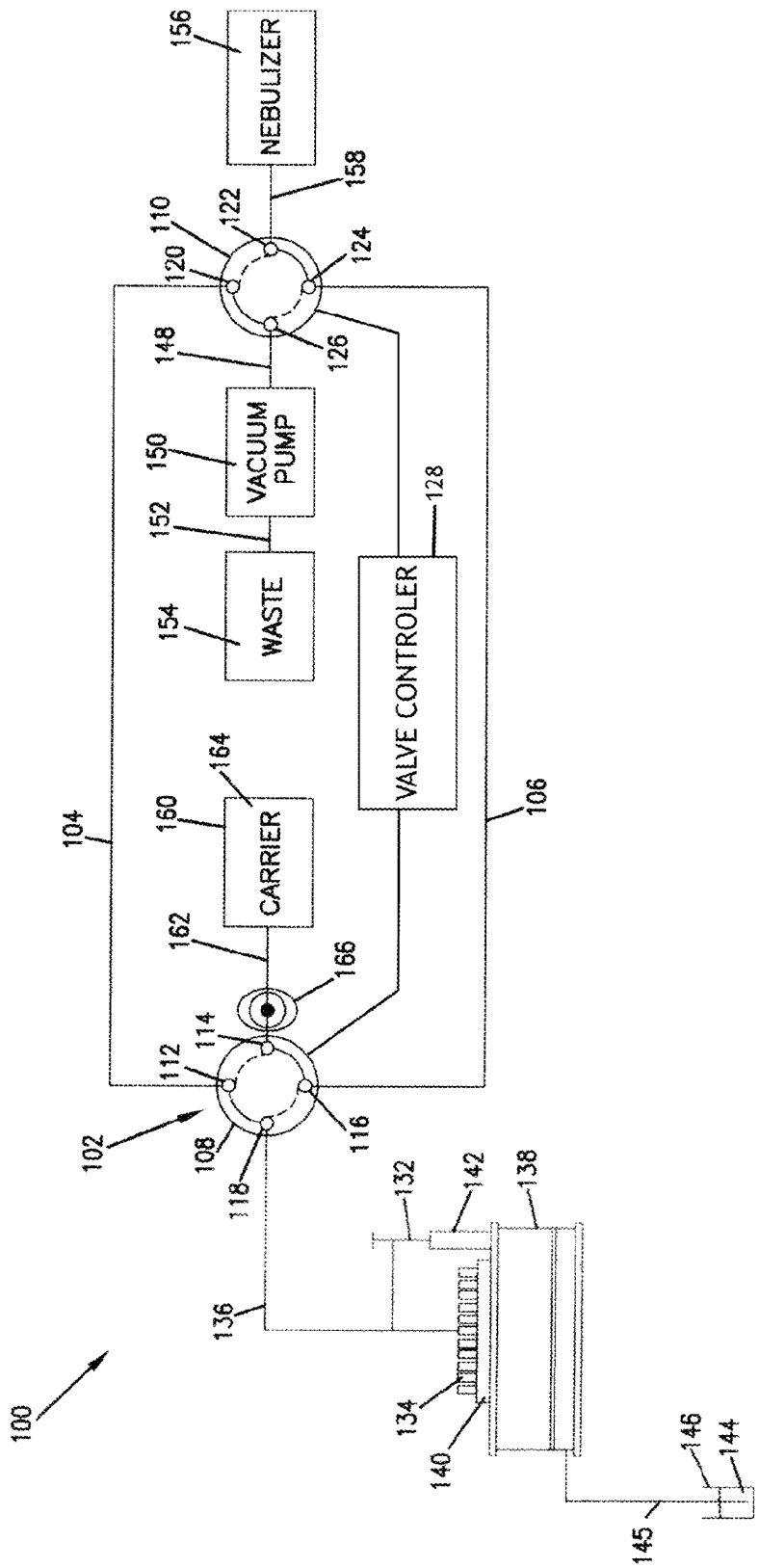
FIG. 1A shows an environment in an example implementation that employs a multiple loop sample introduction system.
Figure 1B:
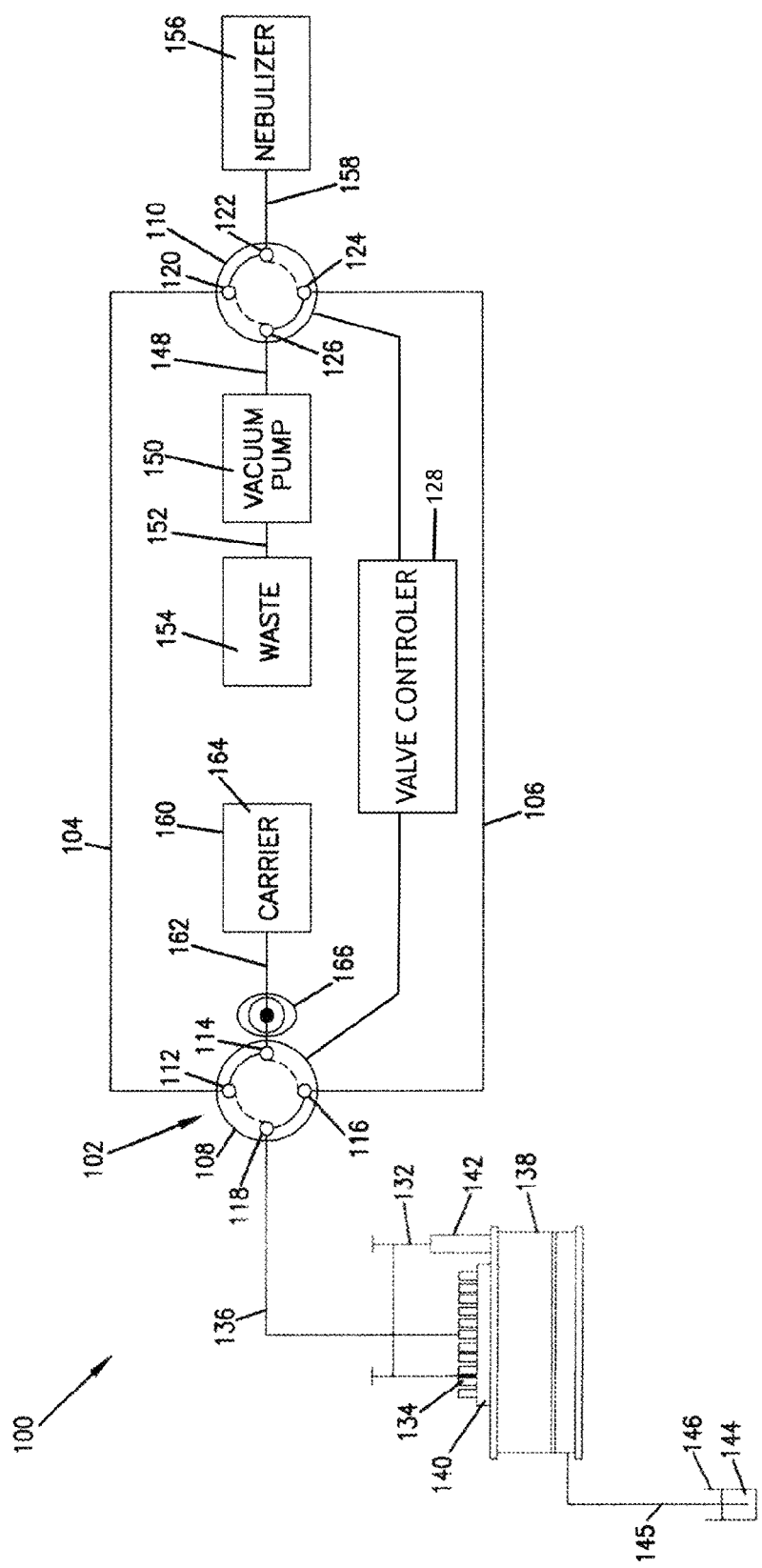
FIG. 1B shows an environment in an example implementation that employs a multiple loop sample introduction system.

FIG. 1A and FIG. 1B shows an environment in an example implementation that employs a multiple loop sample introduction system 100. As shown, the sample introduction system 100 includes a valve assembly 102, a first sample loop 104, and a second sample loop 106. The valve assembly 102 may include a sample collection valve 108 and a sample introduction valve 110. In the embodiment illustrated, the valves 108, 110 comprise rotary valves having at least four ports each (e.g., ports 112, 114, 116 and 118 and ports 120, 122, 124 and 126, respectively). However, it is contemplated that the valves 108, 110 may have other configurations without departing from the scope of the present disclosure, or that the functions of the valves 108, 110 may be combined into a single valve.

The valves 108, 110 may actuate between a first state, shown in FIG. 1A, and a second state, shown in FIG. 1B. When the sample collection valve 108 is actuated to its first state, the valve 108 connects a first port 112 with a fourth port 118 and a second port 114 with a third port 116 to allow flow between the respective pairs of connected ports. Conversely, when the sample collection valve 108 is actuated to its second state, the valve 108 instead connects the first port 112 with the second port 114 and the third port 116 with the fourth port 118 to allow flow between the respective pairs of connected ports. Similarly, when the sample introduction valve 110 is actuated to its first state, the valve 110 connects a first port 120 with a fourth port 126 and a second port 122 with a third port 124 to allow flow between the respective ports. Conversely, when the sample introduction valve 110 is actuated to its second state, the valve 110 instead connects the first port 120 with the second port 122 and the third port 124 with the fourth port 126 to allow flow between the respective pairs of connected ports.

The first and second sample loops 104, 106 are in fluid communication with the sample collection valve 108 and the sample introduction valve 110. For instance, in the implementation illustrated, the first sample loop 104 is coupled to and extends between the first port 112 of the sample collection valve 108 and the corresponding first port 120 of the sample introduction valve 110, while the second sample loop 104 is coupled to and extends between the third port 116 of the sample collection valve 108 and the third port 124 of the sample introduction valve 110. In the embodiment illustrated in FIG. 1A and FIG. 1B, the first and second sample loops 108, 110 may be formed of a suitable material, such as polytetraflouroethylene (PTFE), or the like. However, it is contemplated that the first and second sample loops 108, 110 may have other configurations. For example, in the implementation of the sample introduction system 100 shown in FIG. 2, the first and second sample loops 108, 110 may include columns 228, 230, or like components, that are configured to further process (e.g., filter) the sample.

The sample introduction system 100 may include a separate mechanism to control and coordinate the states of the sample collection valve and the sample introduction valve. Such valve control mechanism may comprise a digital computer to control the state of each valve, a mechanical linkage to operate each valve simultaneously, or any other mechanism suitable to maintain coordinated operation of the valves.

The sample introduction system 100 further includes a probe 132 configured to be inserted into one or more containers 134 that hold liquid samples to be analyzed. The probe 132 is in fluid communication with the sample collection valve 108 via a capillary 136. For example, in the implementation illustrated, the capillary may be coupled to the fourth port 118 of the sample collection valve 108. In embodiments, the capillary 136 may be comprised of tubing formed of suitable material, such as PTFE, or the like.

An autosampler 138 moves the probe 132 among the containers 134 (which are held in a container holder 140 such as a tray or rack) in a predetermined order. The autosampler 138 inserts the probe 132 into each of the containers 134 so that an aliquot of the sample container therein may be withdrawn for analysis. After the probe 132 is withdrawn from a container 134, the autosampler 138 may rinse the probe 132 by inserting the probe 132 into a rinse station 142 containing a suitable rinse fluid 144 drawn from a reservoir 146 of the rinse solution 144 via line 145. The autosampler 138 may provide functionality to control operation of other components of the sample introduction system 100. Control of components of the sample introduction system 100 may also be provided by a separate control module, a general purpose computer, or the like. In the implementation shown, the autosampler 138 may be configured in accordance with one or both of U.S. Pat. Nos. 7,201,072 and 7,469,606, which are herein incorporated by reference in their entireties. However, autosampler 138 having other configurations may be employed.

A vacuum is supplied to the fourth port 126 of the sample introduction valve 110 via line 148 by a vacuum pump 150 coupled to the line 148. In embodiments, the vacuum pump 150 may be configured as a component of the autosampler 138. However, it is contemplated that the vacuum pump 150 may also be a separate component of the sample introduction system 100 such as a control module or the like. A waste line 152 is coupled to the vacuum pump 150 to receive excess sample or rinse fluid. In embodiments, a waste receptacle 154 may be coupled to the waste line 152 to store the excess sample and/or rinse fluid disposal.

In the example implementation shown, a nebulizer 156 is interconnected with the valve assembly 102 via a line 158 coupled to the second port 122 of the sample introduction valve 110. As noted, the nebulizer 156 converts aliquots of sample received from the first and second sample loops 104, 106 into a polydisperse aerosol suitable for ionization in plasma by the ICP spectrometry instrumentation (e.g., ICPMS, ISPAES, of the like). The aerosol is then sorted in a spray chamber to remove larger aerosol particles. Upon leaving the spray chamber, the aerosol is introduced to the ICP spectrometry instrumentation for analysis.

A carrier 160 is furnished via a line 162 coupled to the second port 114 of the sample collection valve 108. The carrier may be supplied from a reservoir 164 by a pump 166 (a peristaltic pump is illustrated) at a predetermined flow rate. The carrier 160 is pumped into the first sample loop 104 or the second sample loop 106 by the pump 166 to transport the aliquots of sample contained therein to the nebulizer 156. The carrier 160 may comprise a fluid that is suitable for use in transport of the particular samples being analyzed. Example carriers 160 include, but are not limited to, liquids such as water, saline solution, oil, or kerosene.

In embodiments, lines 148, 152, 158 and 162 may comprise lengths of flexible tubing formed of a suitable material, such as PTFE, or the like. However, other constructions and materials are possible.

The sample introduction system 100 is configured to allow for the first sample loop 104 to be rinsed and then loaded with an aliquot of a sample while the second sample loop 104 to be rinsed and then loaded with an aliquot of a sample while the second loop 106, already loaded with an aliquot of sample, is concurrently pumped with carrier 160 to introduced the aliquot of sample into the nebulizer 156. The first sample loop 104, now loaded with an aliquot of sample, is then pumped with carrier 128 to introduce the aliquot of sample into the nebulized 156, while the second sample loop 126 concurrently rinsed and then loaded with an aliquot of a new sample. Accordingly, sample introduction system 100 allows one sample to be introduced into the nebulized 156 while a second sample is taken up, thereby reducing the amount of time necessary between analyses of samples. Thus, the throughput of the sample introduction system 100 disclosed may be substantially higher than the throughput of systems employing a single sample loop.

The configuration of the valve assembly 102 allows the sample collection valve 108 to be positioned closer to the probe 132, thereby shortening the capillary 136. This placement reduces the amount of sample used by the system 100 (e.g., reduces the size of the aliquots of sample taken up). The amount of sample required varies depending upon the sample material and the type of analysis. Further, use of a shorter capillary 136 reduces memory effects and absorption of sample by the system 100. Single loop sample introduction systems typically employ capillaries having lengths of about 1.2 meters to about 1.5 meters. While capillaries of other lengths may be used, in some embodiments, the configuration of the valve assembly 102 of the multiple loop sample introduction system 100 allows location of the sample collection valve 108 to facilitate use of a capillary 136 having a length of about 0.5 meters to about 1.2 meters. In one embodiment, the sample introduction system 100 may employ a capillary 136 that is 0.5 meters in length.

Figure 2:
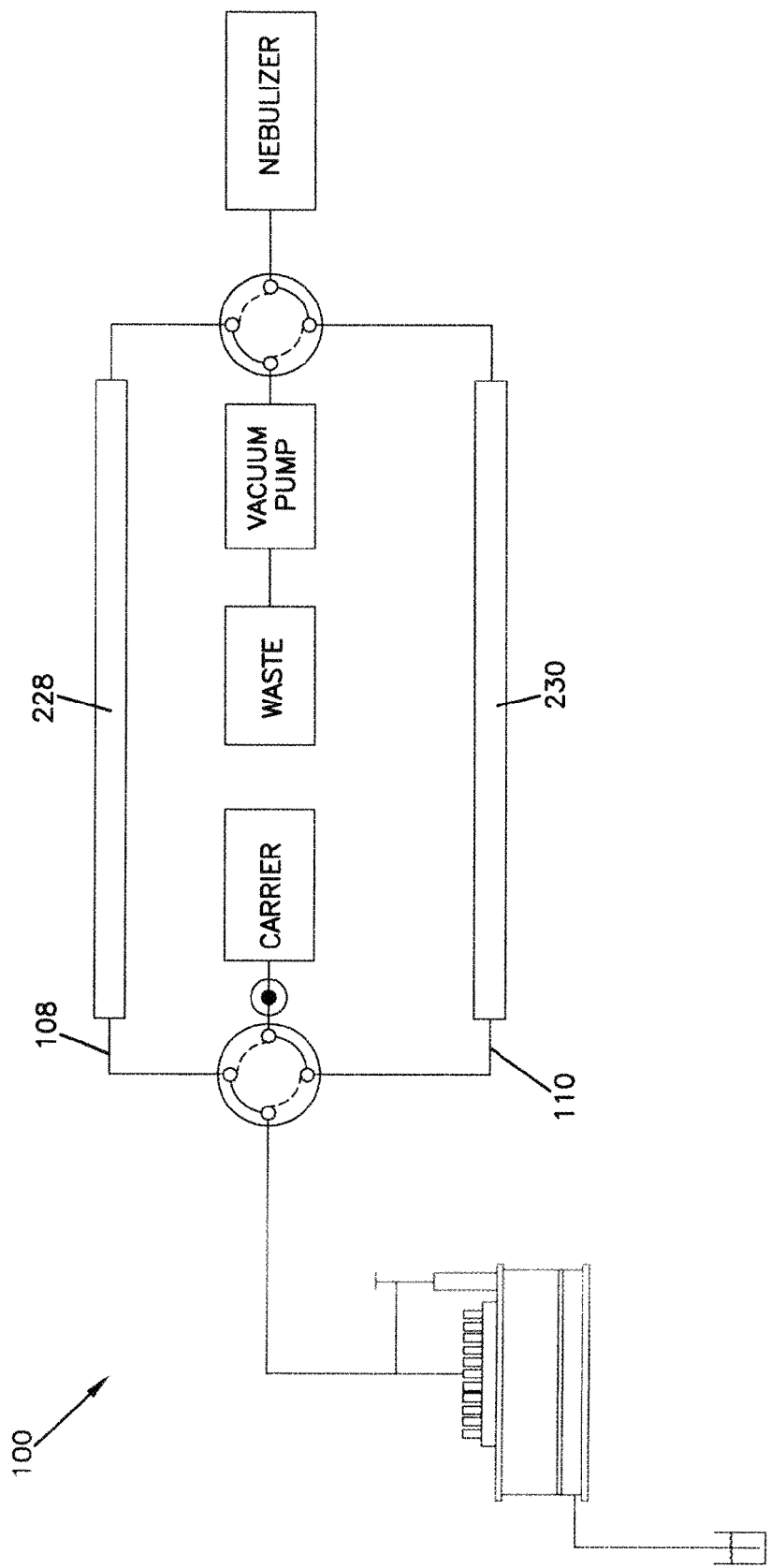
FIG. 2 shows an environment in an example implementation that employs a multiple loop sample introduction system, wherein the sample instruction system employs sample loops comprising columns.
Figure 3:
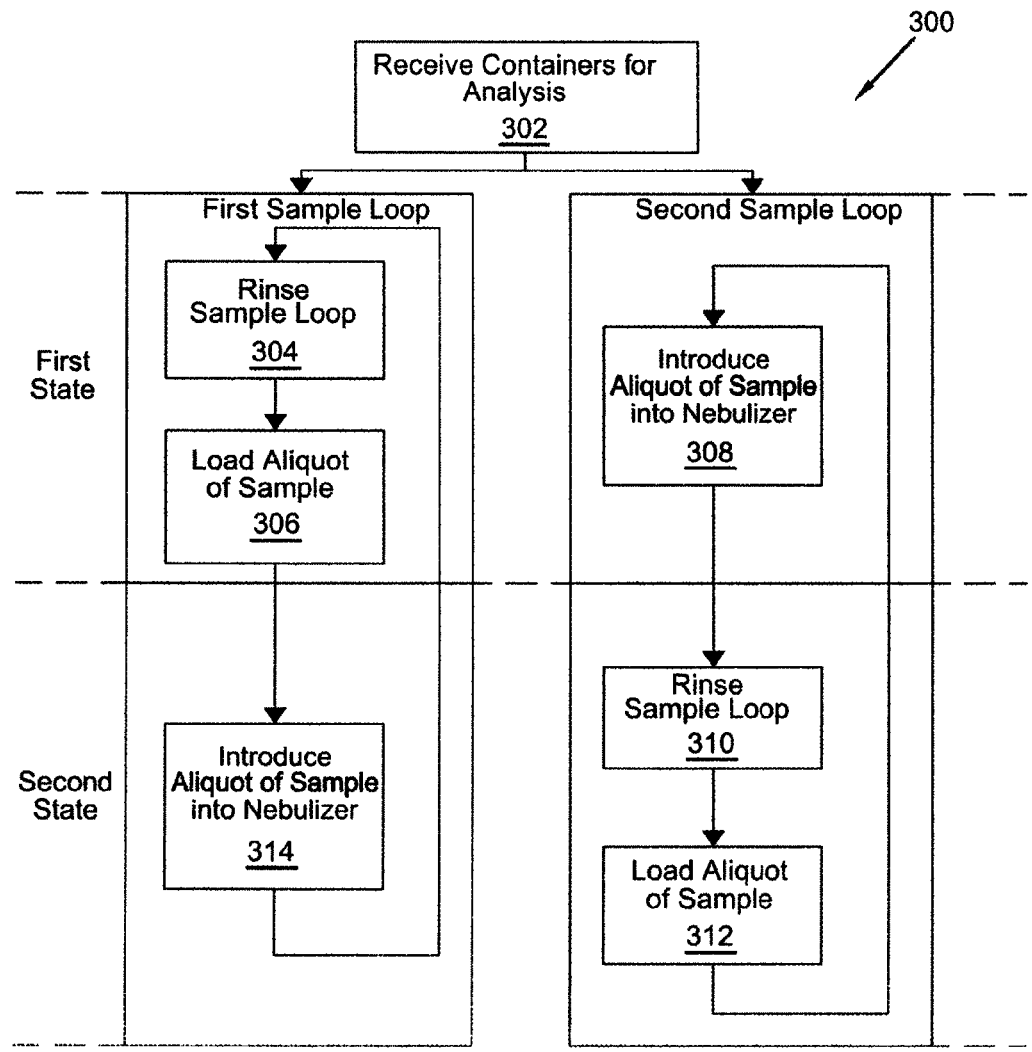
FIG. 3 shows a flow diagram depicting a procedure in an example implementation in which a liquid samples into ICP spectrometry instrumentation by the multiple loop sample introduction system of FIG. 1A and FIG. 1B.

FIG. 3 illustrates an example procedure 300 suitable for use by the sample introduction system 100 of the environments shown in FIG. 1A, FIG. 1B and FIG. 2 to introduce aliquots of liquid samples into a nebulizer. As Shown in FIG. 3, one or more containers holding samples are received for analysis 302. For instance, as shown in FIG. 1A, FIG. 1B and FIG. 2, containers 134 containing various samples to be analyzed may be received in the autosampler 138 in preparation for analysis of the samples by the ICP spectrometry instrumentation.

The first sample loop 104 is rinsed 304 and then loaded with an aliquot of a sample 306. Concurrently, the second sample loop 106, which may already hold an aliquot of a sample, is pumped with carrier 160 to introduce this aliquot of sample into the nebulizer 156 308. For instance, as shown in FIG. 1A, the sample collection valve 108 and the sample introduction valve 110 may each be actuated to the first state so that the sample collection valve 108 and sample introduction valve 110 connect their first port 112, 120 with their fourth port 118, 126 and their second port 114, 122 with their third port 116, 124. A vacuum may then be applied to the first sample loop 104 via the fourth port 126 of the sample introduction valve 110 to draw rinse solution through the first sample loop 104, or to draw an aliquot of sample into the sample loop. For example, the probe 132 may be inserted into the rinse station 142 by the autosampler 136 and the vacuum applied by the vacuum pump 150 to draw rinse fluid through the probe 132, the capillary 136, the sample collection valve 102, and the first sample loop 104. The probe 132 may then be removed from the rinse station 142 and inserted into the sample container 134 by the autosampler 138. A vacuum is then applied by the vacuum pump 150 to draw an aliquot of sample contained in the sample container 134 into the sample loop 104. Excess rinse fluid or sample may be pumped to the waste receptacle 154 for disposal. Concurrently, the carrier 160 is pumped into the second sample loop 106 via the second port 114 of the sample collection valve 108 to transport the aliquot of sample contained therein to the nebulizer 156. In embodiments, additional carrier 160 may be pumped through the sample collection valve 108, second sample loop 106, sample introduction valve 110, and nebulizer 156 after the aliquot of sample is transported to the nebulizer 156 to remove any residue of the sample from these components. Further, it will be understood that, upon initiation of sampling (e.g., when the first sample to be sampled is taken into the first sample loop 106) the second sample loop 106 may initially be empty (e.g., may contain no sample) so that only carrier 160 is introduced into the nebulizer 156.

As shown in FIG. 3, the second sample loop 106 may then be rinsed 310 and loaded with an aliquot of the next sample 312. Concurrently, the first sample loop 104, now loaded with the aliquot of sample 306, is pumped with carrier 160 to introduce the aliquot of sample into the nebulizer 156 314. For instance, as shown in FIG. 1B, the sample collection valve 108 and the sample introduction valve 110 may each be actuated to the second state so that the sample collection valve 108 and sample introduction valve 110 connect their first port 112, 120 with their second port 114, 122 and their third port 116, 124 with their fourth port 118, 126. A vacuum may then be applied to the second sample loop 106 via the fourth port 126 of the sample introduction valve 110 to draw rinse solution through the second sample loop 106, to draw an aliquot of sample into the sample loop 106. For example, the probe 132 may be inserted into the rinse station 142 by the autosampler 138 and the vacuum applied by the vacuum pump 150 to draw rinse fluid through the probe 132, the capillary 136, the sample collection valve 102, and the second loop 106. The probe 132 may then be removed from the rinse station 142 and inserted into a sample container 134 by the autosampler 138. A vacuum is applied by the vacuum pump 150 to draw an aliquot of sample contained in the sample contained 134 into the sample loop 106. Excess rinse fluid or sample may be pumped to the waste receptacle 154 for disposal. Concurrently, carrier 160 is pumped into the first sample loop 104 via the second port 114 of the sample collection valve 108 to transport the aliquot of sample contained therein to the nebulizer 156. In embodiments, additional carrier 160 may be pumped through the sample collection valve 108, first sample loop 104, sample introduction valve 110, and nebulizer 156 after the aliquot of sample is transported to the nebulizer 156 to remove any residue of the sample from these components.

As shown, the procedure 300 may be repeated for analysis of additional samples. The procedure 300 thus alternates between receiving of an aliquot of a sample into the first sample loop 104 304, 306, while concurrently transferring an aliquot of a sample received in the second sample loop 106 to the nebulizer 156 308 and receiving an aliquot of the next sample into the second sample loop 106, 310, 312, while concurrently transferring the aliquot received in the first sample loop 104 304, 306 to the nebulizer 156 314.

It is believed that the present invention and many of its attendant advantages will be understood by the foregoing description, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A sample introduction apparatus comprising:
   a sample collection valve having at least four ports;
   a sample introduction valve having at least four ports;
   a first sample loop, configured to hold an aliquot of liquid sample, functionally connected at one end to a first port of the sample collection valve and at the other end to a first port of the sample introduction valve;
   a second sample loop, configured to hold an aliquot of liquid sample, functionally connected at one end to a third port of the sample collection valve and at the other end to a third port of the sample introduction valve,
   wherein the sample collection valve has a second port connected to a carrier fluid pump and a fourth port connected to a sample collection probe, and the sample introduction valve has a second port connected to a nebulizer and a fourth port connected to a sample loop pump,
   wherein the sample collection valve and the sample introduction valve are configured to alternate between a first state and a second state, and when the sample collection valve is in the first state, the sample introduction valve is in the first state, and when the sample collection valve is in the second state, the sample introduction valve is in the second state,
   wherein when the valves are in the first state, the first port of the sample collection valve is connected to the fourth port of the sample collection valve and the third port of the sample collection valve is connected to the second port of the sample collection valve, and the first port of the sample introduction valve is connected to the fourth port of the sample introduction valve and the third port of the sample introduction valve is connected to the second port of the sample introduction valve, and the sample collection probe is in fluid communication with the sample loop pump through the first sample loop and the carrier fluid pump is in fluid communication with the nebulizer through the second sample loop, wherein when the valves are in the second state, the first port of the sample collection valve is connected to the second port of the sample collection valve and the third port of the sample collection valve is connected to the fourth port of the sample collection valve, and the first port of the sample introduction valve is connected to the second port of the sample introduction valve and the third port of the sample introduction valve is connected to the fourth port of the sample introduction valve, and the sample collection probe is in fluid communication with the sample loop pump through the second sample loop and the carrier fluid pump is in fluid communication with the nebulizer through the first sample loop.

2. The apparatus of claim 1, further comprising: a valve controller functionally connected to the sample collection valve and the sample introduction valve, wherein the valve controller is configured to alternate the sample collection valve and the sample introduction valve between the first state and the second state.

3. The apparatus of claim 1, further comprising:

a carrier fluid reservoir configured to hold carrier fluid, functionally connected to the carrier fluid pump.

4. The apparatus of claim 1, further comprising: a waste receptacle connected to the sample loop pump, wherein the waste receptacle receives an excess sample amount or a rinse fluid amount.

5. The apparatus of claim 1, wherein the sample collection probe is comprised of:

a capillary having a first end connected to the fourth valve of the sample collection valve;

a probe having a first end connected to the second end of the capillary; and an autosampler accessible by a second end of the probe, wherein the autosampler has a sample container holder disposed on a surface of the autosampler and configured to hold a plurality of liquid sample containers, and the autosampler and the probe are configured such that the probe can access each of the plurality of liquid sample containers to retrieve an aliquot of a liquid sample from one or more containers.

6. The apparatus of claim 5, further comprising:

a probe rinsing station having a rinse fluid reservoir configured to hold a rinse fluid, wherein the rinse fluid is accessible by the second end of the probe, and the probe rinsing station is disposed on the surface of the autosampler.

7. The apparatus of claim 6, wherein a supply reservoir containing a supply of rinse fluid is in fluid communication with the rinse fluid reservoir through a line, wherein rinse fluid is drawn from the supply reservoir to the rinse fluid reservoir.

8. The apparatus of claim 1, wherein the sample loop pump is a vacuum pump.

9. The apparatus of claim 1, wherein at least one of the first and second sample loops have a fluid containment column disposed inline between the ports of the sample collection valve and the sample introduction valve, respectively.

10. A sample introduction apparatus comprising:

a plurality of sample loops;

a sample collection assembly comprising:

a sample collection means, functionally connected to a first sample loop of the plurality of sample loops; and a sample loop pumping means, functionally connected to the first sample loop;

a sample introduction assembly comprising:

a carrier fluid pumping means, functionally connected to a second sample loop of the plurality of sample loops; and a nebulizing means, functionally connected to the second sample loop;

a first sample loop switching means functionally connected to the sample collection means, the carrier fluid pumping means, and the plurality of sample loops; and a second sample loop switching means functionally connected to the sample loop pumping means, the nebulizing means, and the plurality of sample loops, wherein the first sample loop switching means is configured to disconnect the first sample loop from the sample collection means and to disconnect the second sample loop from the carrier fluid pumping means, and to functionally connect the first sample loop to the carrier fluid pumping means and the second sample loop to the sample collection means, while the second sample loop switching means is configured to disconnect the first sample loop from the sample loop pumping means and the second sample loop from the nebulizing means, and to functionally connect the first sample loop to the nebulizing means and the second sample loop to the sample loop pumping means.

11. The apparatus of claim 10, further comprising: a sample loop switching control means functionally connected to the first sample loop switching means and the second sample loop switching means, wherein the sample loop switching control means is configured to alternate the first sample loop switching means between a first state where the first sample loop switching means is configured to connect the first sample loop to the sample collection means and the second sample loop to the carrier fluid pumping means, and where the second sample loop switching means is configured to connect the first sample loop to the sample loop pumping means and the second sample loop to the nebulizing means; and a second state where the first sample loop switching means is configured to connect the second sample loop to the sample collection means and the first sample loop to the carrier fluid pumping means, and where the second sample loop switching means is configured to connect the second sample loop to the sample loop pumping means and the first sample loop to the nebulizing means.

12. The apparatus of claim 10, further comprising: a waste fluid receiving means, configured to receive excess liquid sample and rinse fluid, functionally connected to the sample loop pumping means.

13. The apparatus of claim 10, further comprising: an automatic sample selection means, configured to automatically position the sample collection means to retrieve a liquid sample from a plurality of liquid sample containers, in proximity to the sample collection means.

14. The apparatus of claim 13, further comprising: a rinsing means, configured hold a rinse fluid, disposed on a surface of the automatic sample selection means, wherein the rinsing means is accessible to the sample collection means.

15. The apparatus of claim 10, wherein at least one of the plurality of sample loops comprises a column.

16. A sample introduction apparatus comprising:
a first sample loop switching mechanism configured to alternate between a first state in which the first sample loop switching mechanism is configured to connect a first sample loop to a carrier fluid pump and a second sample loop to a sample collecting probe, and a second state in which the first sample loop switching mechanism is configured to connect the first sample loop to the sample collecting probe and the second sample loop to the carrier fluid pump;
a second sample loop switching mechanism configured to alternate between the first state in which the second sample loop switching mechanism is configured to connect the first sample loop to a nebulizer and the second sample loop to a sample loop pump, and the second state in which the second sample loop switching mechanism is configured to connect the first sample loop to the sample loop pump and the second sample loop to the nebulizer;
a first sample loop, configured to temporarily hold and port an aliquot of liquid sample, the first sample loop functionally connected at one end to the first sample loop switching mechanism and functionally connected at the other end to the second sample loop switching mechanism; and
a second sample loop, configured to temporarily hold and port an aliquot of liquid sample, the second sample loop functionally connected at one end to the first sample loop switching mechanism and functionally connected at the other end to the second sample loop switching mechanism,
wherein the first sample loop switching mechanism and the second sample loop switching mechanism are configured to synchronously alternate such that when the first sample loop switching mechanism is in the first state, the second sample loop switching mechanism is in the first state, and when the first sample loop switching mechanism is in the second state, the second sample loop switching mechanism is in the second state.

17. The apparatus of claim 16, further comprising: a sample loop switching mechanism control means, configured to alternate the first sample loop switching mechanism between the first state and the second state, while synchronously alternating the second sample loop switching mechanism between the first state and the second state.

18. A sample introduction apparatus comprising:
a sample collection valve;
a sample introduction valve;
a first sample loop, configured to hold an aliquot of liquid sample, functionally connected at one end to the sample collection valve and at the other end to the sample introduction valve;
a second sample loop, configured to hold an aliquot of liquid sample, functionally connected at one end to the sample collection valve and at the other end to the sample introduction valve;
a carrier fluid reservoir configured to hold a carrier fluid;
a carrier fluid pump configured to pump carrier fluid from the carrier fluid reservoir into the sample collection valve;
a sample collection probe functionally connected to the sample collection valve;
an automatic sample selection apparatus, configured to position the sample collection probe to retrieve liquid sample from a plurality of liquid sample containers, in proximity to the sample collection probe;
a sample collection probe rinse station, configured to receive the sample collection probe, the station disposed on a surface of the automatic sample selection apparatus;
a sample collection probe rinse fluid reservoir, configured to hold a sample collection probe rinse fluid, functionally connected to the sample collection probe rinse fluid station;
a sample loop pump functionally connected to the sample introduction valve;
a waste fluid receptacle, configured to receive waste fluid, functionally connected to the sample loop pump; and
a nebulizer functionally connected to the sample introduction valve, wherein the sample collection valve is configured to alternate between a first state connecting the first sample loop to the sample collection probe and the second sample loop to the carrier fluid pump, and a second state connecting the first sample loop to the carrier fluid pump and the second sample loop to the sample collection probe; while the sample introduction valve is configured to alternate between the first state connecting the first sample loop to the sample loop pump and the second sample loop to the nebulizer, and the second state connecting the first sample loop to the nebulizer and the second sample loop to the sample loop pump.

* * * * *